(12) United States Patent
Guimberteau et al.

(10) Patent No.: US 12,257,226 B2
(45) Date of Patent: Mar. 25, 2025

(54) VETERINARY COMPOSITIONS AND THE USES THEREOF FOR CONTROLLING IRON DEFICIENCIES IN NON-HUMAN MAMMALS

(71) Applicant: Ceva Sante Animale, Libourne (FR)

(72) Inventors: Florence Guimberteau, Libourne (FR); Hamadi Karembe, Libourne (FR)

(73) Assignee: Ceva Sante Animale, Libourne (FR)

( * ) Notice: Subject to any disclaimer, the term of this patent is extended or adjusted under 35 U.S.C. 154(b) by 936 days.

(21) Appl. No.: 17/055,869

(22) PCT Filed: May 16, 2019

(86) PCT No.: PCT/EP2019/062700
§ 371 (c)(1),
(2) Date: Nov. 16, 2020

(87) PCT Pub. No.: WO2019/219855
PCT Pub. Date: Nov. 21, 2019

(65) Prior Publication Data
US 2021/0220319 A1   Jul. 22, 2021

(30) Foreign Application Priority Data
May 16, 2018 (EP) .................... 18305607

(51) Int. Cl.
| | | |
|---|---|---|
| A61K 31/295 | (2006.01) | |
| A61K 9/00 | (2006.01) | |
| A61K 31/7135 | (2006.01) | |
| A61K 31/721 | (2006.01) | |
| A61K 47/02 | (2006.01) | |
| A61K 47/10 | (2017.01) | |
| A61K 47/20 | (2006.01) | |
| A61K 47/32 | (2006.01) | |

(52) U.S. Cl.
CPC .......... *A61K 31/295* (2013.01); *A61K 9/0019* (2013.01); *A61K 31/7135* (2013.01); *A61K 31/721* (2013.01); *A61K 47/02* (2013.01); *A61K 47/10* (2013.01); *A61K 47/20* (2013.01); *A61K 47/32* (2013.01)

(58) Field of Classification Search
CPC .............. A61K 31/295; A61K 31/7135; A61K 31/721; A61P 7/06
USPC ......................................................... 514/59
See application file for complete search history.

(56) References Cited

U.S. PATENT DOCUMENTS

| | | | |
|---|---|---|---|
| 3,536,696 A * | 10/1970 | Alsop ................. | A61K 31/295 536/112 |
| 2007/0065521 A1 * | 3/2007 | Venkataraman ..... | A61K 31/555 514/185 |
| 2013/0109662 A1 | 5/2013 | Bark et al. | |
| 2015/0313940 A1 | 11/2015 | Le Meur et al. | |

FOREIGN PATENT DOCUMENTS

| | | |
|---|---|---|
| JP | S53148538 A | 12/1978 |
| JP | 2010528996 A | 8/2010 |
| JP | 2016505558 A | 2/2016 |
| RU | 2079305 C1 | 5/1997 |
| RU | 2257213 C2 | 7/2005 |

* cited by examiner

*Primary Examiner* — Ganapathy Krishnan
(74) *Attorney, Agent, or Firm* — Wood, Phillips, Katz, Clark & Mortimer

(57) ABSTRACT

The present invention relates to a veterinary composition comprising an iron complex as a sole active ingredient and a water-soluble polymer. The invention further relates to the use of such composition for controlling iron deficiencies and/or anaemic states in a non-human mammal.

30 Claims, No Drawings

VETERINARY COMPOSITIONS AND THE USES THEREOF FOR CONTROLLING IRON DEFICIENCIES IN NON-HUMAN MAMMALS

FIELD OF THE INVENTION

The present invention belongs to the veterinary field and relates to formulations comprising iron. The invention further relates to the use of such formulations for controlling iron deficiencies and/or anaemic states in a non-human mammal.

BACKGROUND OF THE INVENTION

Newborn animals are liable to anemia caused by iron deficiency within a short period of time after their birth. They are born with very low iron reserves and receive too little iron from breast milk to ensure a good growth. For instance in the pig industry, the piglet is born with limited stores of iron and if it had been born in the wild would depend on supplementation to its diet from iron bearing soils. Indoors, the piglet has no access to iron source other than to the sows' milk (which is iron-deficient) until it starts to eat creep feed. The piglet is born with a normal level of haemoglobin in the blood of 12-13 g/100 mL and this rapidly drops down to 6-7 g/100 mL by 10 to 14 days of age. A shortage of iron results in lowered levels of haemoglobin in the red cells (anemia), a lowered capacity for the carriage of oxygen around the body, an increased susceptibility to disease, and low or poor bodyweight development. Severe iron deficiency anemia may also lead to the young pig's death.

Therefore, it is necessary to give extra iron to the newborn piglet to overcome iron deficiencies. In this context, a series of quite different iron formulations, which differ both in the type of iron compound and in the mode of application, are commercially available for preventing iron deficiency anemia.

For instance, Pharmacosmos and Ark Animal Care Ltd. provide an injectable solution containing iron(III) dextran, which is commercialized under the trademark Uniferon® and Anaemex®. Ceva Santé Animale, SerumWerk and Labiana provide an injectable solution comprising an aqueous colloidal solution of beta-ferric oxyhydroxide and dextran glucoheptonic acid (Gleptoferron commercialized under the trademark Gleptosil®, Ursoferran®, and Gleptoferron 200 Labiana).

However, with the increase in litter size (hyperprolific sows) and fast growing piglets, the above commercially available formulations administered in piglets do not always meet the farmer's expectations and cannot prevent a total efficacy for preventing anemia in piglets. Therefore, an increase in the dose rate and/or a second injection before or at weaning is recommended by some iron suppliers. The increase in dose rate is limited by the potential toxicity of the iron in young animals. The second injection is labour intensive and less effective. This is due to the fact that the hematinic activity of oral or injected iron decreases with the age. Therefore, it is generally recommended to treat the animals within the first 3 days of life.

Thus, there remains today a need to develop new formulations of iron having an improved efficacy for controlling iron deficiencies and/or anaemic states in a non-human mammal.

SUMMARY OF THE INVENTION

In this context, the inventors propose a veterinary composition comprising an iron complex combined to a water-soluble polymer.

The present invention therefore relates to a veterinary composition comprising an iron complex as a sole active ingredient and a water-soluble polymer.

In a particular embodiment, said water-soluble polymer is chosen among polyvinyl pyrrolidone, polyvinyl alcohol, polyacrylic acid, polyacrylamides, N-(2-hydroxypropyl) methacrylamide, divinyl ether-maleic anhydride, polyoxazoline, polyphosphates, polyphosphazenes, and a mixture thereof, and is preferably polyvinyl pyrrolidone.

In a preferred embodiment, said water-soluble polymer is in a concentration from 1 to 100 mg/mL, preferably from 5 to 70 mg/mL, more preferably from 7 to 60 mg/mL, even more preferably from 10 to 50 mg/mL.

In a further particular embodiment, the veterinary composition further comprises an organic solvent, preferably in a concentration from 1 to 20 mg/mL, more preferably from 5 to 10 mg/mL, even more preferably from 5 to 8 mg/mL.

In a further particular embodiment, the veterinary composition further comprises a pharmaceutically acceptable salt and/or a surfactant having an HLB greater than 8.

In a preferred embodiment, said pharmaceutically acceptable salt is in a concentration from 1 to 100 mg/mL, preferably from 5 to 70 mg/mL, more preferably from 10 to 50 mg/mL.

In a further preferred embodiment, said surfactant having an HLB greater than 8 is in a concentration from 0.01 to 10 mg/mL, preferably from 0.5 to 8 mg/mL, more preferably from 1 to 5 mg/mL.

In a further particular embodiment, said iron complex is chosen among an iron(2+) carboxylic acid complex, an iron(3+) carboxylic acid complex, an iron(2+) chelate complex with amino acids, an iron(3+) chelate complex with amino acids, a polynuclear iron(3+) polysaccharide complex, and a mixture thereof.

In a preferred embodiment, said polynuclear iron(3+) polysaccharide complex is chosen among an aqueous colloidal solution of beta-ferric oxyhydroxide and dextran glucoheptonic acid, iron(III) dextran, iron(III) hydroxy polymaltose, and is preferably an aqueous colloidal solution of beta-ferric oxyhydroxide and dextran glucoheptonic acid.

In a further preferred embodiment, the concentration of iron supplied as iron complex is in a concentration from 50 to 300 mg/mL iron element, preferably from 100 to 200 mg/mL, more preferably from 120 to 150 mg/mL.

A further object of the invention is a veterinary composition as disclosed herein for use for controlling iron deficiencies and/or anaemic states in a non-human mammal.

In a preferred embodiment, said non-human mammal is a porcine, an ovine, a bovine, a canine, or a feline, and is preferably a piglet.

In a further preferred embodiment, said composition for use is administered by injection, preferably by intramuscular injection.

DETAILED DESCRIPTION OF THE INVENTION

The inventors provide a veterinary composition comprising an iron complex as a sole active ingredient and a water-soluble polymer. The presence of an effective amount of a water-soluble polymer in the composition may increase the hematinic efficacy and improve the tissue distribution of the iron complex in the non-human mammal. The compositions of the invention thus can exhibit an improved efficacy in the control of iron deficiencies and/or anaemic states in a non-human mammal compared to the iron formulations currently used. The compositions of the invention may also be well tolerated and may improve the bodyweight development of the non-human mammal.

Composition

The present invention thus provides a veterinary composition comprising an iron complex as a sole active ingredient and a water-soluble polymer.

According to the invention, the iron complex is the sole active ingredient. The compositions of the invention thus comprise no further active ingredient, such as anti-infectious agents, like triazines, antibiotics, anthelmintics, endectocides, anti-inflammatory agents, and vitamins.

As used herein, "an iron complex" includes any form of iron(2+) or 3(+) complexes. In a particular embodiment, the iron complex is chosen among iron(2+) carboxylic acid complex, iron(3+) carboxylic acid complex, iron(2+) chelate complexes with amino acids, iron(3+) chelate complexes with amino acids, polynuclear iron(3+) polysaccharide complex, and the mixture thereof.

Iron(2+) or −(3+) carboxylic acid complexes, and iron (2+) or −(3+) chelate complexes with amino acids are complexed in a chelate-like manner. They form relatively stable iron complexes which are only partly broken down into the ions by the gastric acid. Examples of iron(2+) carboxylic acid complexes which may be mentioned without limitation are, for instance, iron(II) lactate, iron(II) gluconate, or iron(II) fumarate, or hydrates thereof. Examples of iron(3+) carboxylic acid complexes include, for instance, iron(III) citrate, ammonium iron(III) citrate, or hydrates thereof. As an example of iron(2+) chelate complexes with amino acids, iron(II) bisglycinate, iron(II) methionate, and hydrates thereof may be cited.

Polynuclear iron(3+) polysaccharide complexes are understood as meaning complexes of the iron(3+) ion with hydroxide ions (OH$^-$), aqueous groups (H$_2$O) and oxygen (O) which are present in oligomeric or polymeric form and which are associated in their coordination sphere as complexes with one or more than one of the above oligomeric and polymeric carbohydrate compounds. Polynuclear iron (3+) polysaccharide complexes thus also include polynuclear iron(3+) hydroxide polysaccharide complexes and polynuclear iron(3+) oxyhydroxy polysaccharide complexes. Examples of polynuclear iron(3+) polysaccharide complexes include, with no limitation, polynuclear iron(III) polysaccharide complex compounds in which a polynuclear β-FeO(OH) nuclear complex contains polymeric carbohydrate compounds associated at the free coordination sites, such as iron dextran(III), glucoheptonic acid of iron(III) dextran, iron(III) isomaltoside, iron(III) carboxymaltose, iron(III) hydroxy polymaltose, iron(III) sucrose, or iron(III) oligosaccharide.

In a preferred embodiment, the polynuclear iron(3+) polysaccharide complex of the compositions of the invention is chosen among an aqueous colloidal solution of beta-ferric oxyhydroxide and dextran glucoheptonic acid, iron(III) dextran, and iron(III) hydroxy polymaltose. In a more preferred embodiment, the polynuclear iron(3+) polysaccharide complex is an aqueous colloidal solution of beta-ferric oxyhydroxide and dextran glucoheptonic acid (Gleptoferron commercialized under the trademark Gleptosil® or Ursoferran®). In a further more preferred embodiment, the polynuclear iron(3+) polysaccharide complex is a ferric hydroxide with a low molecular weight dextran, such as the product commercialized under the trademark Uniferon® or Dexafer®; or a ferric hydroxide with macromolecular dextran, such as the product commercialized under the trademark Ferroforte®.

In a particular embodiment, the concentration of iron supplied from iron complex as disclosed herein is in a concentration from 50 to 300 mg/mL iron element, preferably from 100 to 200 mg/mL, more preferably from 120 to 150 mg/mL. In a more preferred embodiment, the concentration of iron supplied as iron complex is in an amount of about 50, 100, 133, 133.3, 133.4, 133.5, 150, 200, 250, 300 mg iron element per mL of composition. In a further more preferred embodiment, the concentration of iron supplied as iron complex is in an amount of about 133.4 mg iron element per mL of composition or about 200 mg iron element per 1.5 mL of composition.

According to the invention, the concentration of iron supplied as or in the form of iron complex in the composition corresponds to the concentration of the iron element. It is thus well understood that the concentration of the iron complex in the composition may vary depending on the nature of the complex. A skilled person can easily adapt the concentration of iron complex knowing the concentration of the iron element to be added in the composition.

Water-soluble polymers are natural or synthetic substances that dissolve, disperse, or swell in water and, thus, modify the physical properties of aqueous systems in the form of gelation, thickening or emulsification/stabilization. They have repeating units or blocks of units forming a polymer chain that contains hydrophilic groups which substitute the polymer chain or are incorporated into the backbone of the polymer chain.

Preferred water-soluble polymers of the invention are chosen among polyvinyl pyrrolidone, polyvinyl alcohol, polyacrylic acid, polyacrylamides, N-(2-hydroxypropyl) methacrylamide, divinyl ether-maleic anhydride, polyoxazoline, polyphosphates, polyphosphazenes, and a mixture thereof. In a more preferred embodiment, the water-soluble polymer is polyvinyl pyrrolidone (Povidone).

In a particular embodiment, the water-soluble polymer as disclosed herein is in a concentration from 1 to 100 mg/mL, preferably from 5 to 70 mg/mL, more preferably from 7 to 60 mg/mL, even more preferably from 10 to 50 mg/mL. In a more preferred embodiment, the water-soluble polymer is in an amount of about 6, 7, 8, 9, 10, 11, 12, 13, 14, 15, 20, 25, 30, 35, 40, 45, 46, 47, 48, 49, 50, 51, 52, 53, 54, or 55 mg per mL of composition. In a further more preferred embodiment, the water-soluble polymer is in an amount of about 10 or 50 mg per mL of composition or about 15 or 75 mg per 1.5 mL of composition.

A preferred composition according to the invention is a veterinary composition comprising:
- a concentration from 50 to 300 mg/mL, preferably from 100 to 200 mg/mL, more preferably from 120 to 150 mg/mL of iron element supplied as iron complex as a sole active ingredient as disclosed herein; and
- a concentration from 1 to 100 mg/mL, preferably from 5 to 70 mg/mL, preferably from 7 to 60 mg/mL, more preferably from 10 to 50 mg/mL of a water-soluble polymer as disclosed herein.

A more preferred composition according to the invention is a veterinary composition comprising:
- a concentration of about 133.4 mg/mL of iron element supplied as iron complex as a sole active ingredient as disclosed herein; and
- a concentration of about 10 or 50 mg/mL of polyvinyl pyrrolidone.

The term "about" will be understood by those skilled in the art and can vary to a certain extent according to the context in which it is used. If some uses of this term are not clear for those skilled in the art depending on the context, "about" means plus or minus 20%, preferably plus or minus 10% of the specific term.

As disclosed herein, the ranges "from X to Y" or "between X and Y" include the terms "X" and "Y".

In a further particular embodiment, the veterinary composition comprises an iron complex as disclosed herein as a sole active ingredient and a water-soluble polymer as disclosed herein, in which the weight ratio from the iron element supplied as iron complex to the water-soluble polymer is comprised between 0.5 and 300, preferably between 1.5 and 40, 2 and 20, 2.4 and 15, more preferably between 2.7 and 13.3, even more preferably about 2.7 or about 13.3.

In a further particular embodiment, the veterinary composition as disclosed herein further comprises an organic solvent. Preferably the organic solvent is chosen among methanol, ethanol, butanol, ethylene glycol, polyethylene glycol, propylene glycol, polypropylene glycol, glycerol, phenol, benzyl alcohol, phenylethanol, phenoxyethanol, ethyl acetate, butyl acetate benzyl benzoate, ethyl oleate, diethylene glycol monoethyl ether, diethylene glycol monobutyl ether, dipropylene glycol monomethyl ether, acetone, methyl ethyl ketone, glycerol formal, 2,2-dimethyl-4-hydroxymethyl-1,3-dioxolane, N-methyl-pyrrolidone, 2-pyrrolidone, N,N-dimethylacetamide, glycofurol, dimethyl-isosorbitol, lauroglycol, propylene carbonate, octyldodecanol, dimethylformamide, and a mixture thereof. More preferably, the organic solvent is phenol.

In a preferred embodiment, the organic solvent is in a concentration from 1 to 20 mg/mL, preferably from 5 to 10 mg/mL, more preferably from 5 to 8 mg/mL. In a more preferred embodiment, the organic solvent is in an amount of about 6.4 mg per mL of composition or about 9.6 mg per 1.5 mL of composition.

A preferred composition according to the invention is a veterinary composition comprising:
  a concentration from 50 to 300 mg/mL, preferably from 100 to 200 mg/mL, more preferably from 120 to 150 mg/mL of iron element supplied as iron complex as a sole active ingredient as disclosed herein;
  a concentration from 1 to 100 mg/mL, preferably from 5 to 70 mg/mL, preferably from 7 to 60 mg/mL, more preferably from 10 to 50 mg/ml of a water-soluble polymer as disclosed herein; and
  a concentration from 1 to 20 mg/mL, preferably from 5 to 10 mg/mL, more preferably from 5 to 8 mg/mL of an organic solvent as disclosed herein.

A more preferred composition according to the invention is a veterinary composition comprising:
  a concentration of about 133.4 mg/mL of iron element supplied as iron complex as a sole active ingredient as disclosed herein;
  a concentration of about 10 or 50 mg/mL of polyvinyl pyrrolidone; and
  a concentration of about 6.4 mg/mL of phenol.

Further Excipients

The veterinary composition of the invention may further comprise at least one excipient such as a pharmaceutically acceptable salt and/or a surfactant, particularly a surfactant having an HLB greater than 8.

An object of the invention is thus a veterinary composition as disclosed herein, further comprising a pharmaceutically acceptable salt and/or a surfactant having an HLB greater than 8.

In a preferred embodiment, the veterinary composition of the invention further comprises a pharmaceutically acceptable salt.

As used herein, "a pharmaceutically acceptable salt" includes both organic salts and inorganic salts. Representative examples of organic salts comprise, for instance, formates, acetates, trichloroacetates, propionates, benzoates, gluconates, carbonates, citrates, cinnamates, fumarates, maleates and methanesulfonates. Representative examples of inorganic salts comprise, for instance, hydrochlorides, hydrobromides, iodates, ammonium, sulfonates and phosphates. In a particular embodiment of the invention, the pharmaceutically acceptable salt includes any water-soluble agent providing an ionic strength.

In a preferred embodiment, the pharmaceutically acceptable salt is chosen among calcium gluconate, calcium phosphate, calcium chloride, calcium sulfate, calcium carbonate, magnesium gluconate, magnesium phosphate, magnesium chloride, magnesium sulfate, magnesium carbonate, potassium phosphate, potassium gluconate, potassium chloride, potassium sulfate, potassium carbonate, sodium gluconate, sodium chloride, sodium carbonate, sodium lactate, sodium propionate, sodium phosphate, sodium citrate, sodium sulfate, ammonium chloride, ammonium carbonate, and a mixture thereof. In a more preferred embodiment, the pharmaceutically acceptable salt is sodium chloride.

In a particular embodiment, the pharmaceutically acceptable salt as disclosed herein is in a concentration from 1 to 100 mg/mL. In a particular embodiment, the pharmaceutically acceptable salt as disclosed herein is in a concentration from 5 to 70 mg/mL, preferably from 7 to 60 mg/mL, more preferably from 10 to 50 mg/mL. In a more preferred embodiment, the pharmaceutically acceptable salt is in an amount of about 6, 7, 8, 9, 10, 11, 12, 13, 14, 15, 20, 25, 30, 35, 40, 45, 46, 47, 48, 49, 50, 51, 52, 53, 54, or 55 mg per mL of composition. In a further more preferred embodiment, the pharmaceutically acceptable salt is in an amount of about 10 or 50 mg per mL of composition or about 15 or 75 mg per 1.5 mL of composition.

A preferred composition according to the invention is a veterinary composition comprising:
  a concentration from 50 to 300 mg/mL, preferably from 100 to 200 mg/mL, more preferably from 120 to 150 mg/mL of iron element supplied as iron complex as a sole active ingredient as disclosed herein;
  a concentration from 1 to 100 mg/mL, preferably from 5 to 70 mg/mL, preferably from 7 to 60 mg/mL, more preferably from 10 to 50 mg/mL of a water-soluble polymer as disclosed herein;
  a concentration from 1 to 20 mg/mL, preferably from 5 to 10 mg/mL, more preferably from 5 to 8 mg/mL of an organic solvent as disclosed herein; and
  a concentration from 1 to 100 mg/mL, preferably from 5 to 70 mg/mL, more preferably from 10 to 50 mg/mL of a pharmaceutically acceptable salt as disclosed herein.

A more preferred composition according to the invention is a veterinary composition comprising:
  a concentration of about 133.4 mg/mL of iron element supplied as iron complex as a sole active ingredient as disclosed herein;
  a concentration of about 10 or 50 mg/mL of polyvinyl pyrrolidone;
  a concentration of about 6.4 mg/mL of phenol; and
  a concentration of about 10 or 50 mg/mL of sodium chloride.

It is well understood that the above concentrations or amounts of the pharmaceutically acceptable salt correspond to the concentrations or amounts which have been added to prepare the compositions of the invention. In other terms, such concentrations or amounts do not include the possible impurities obtained during the processes of preparation of the iron complex, and that may be recovered in the original raw material.

In a further preferred embodiment, the veterinary composition of the invention further comprises a surfactant having an HLB greater than 8.

The term "surfactant" designates an agent that modifies the liquid surface tension, in particular that of water. A surfactant molecule can be described as a hydrophobic chain (affinity for non-polar solvents) linked to a hydrophilic chain (affinity for polar solvents). Thus, surfactants present antagonistic properties and, once formulated in water, the hydrophobic parts rejects the molecule on the surface and the hydrophilic part tends to plunge within the liquid.

The HLB (Hydrophilic-Lipophilic Balance) is used to determine the hydrophilic or hydrophobic dominant character of a surfactant. HLB values have been proposed in 1949 by Griffin (Griffin WC, Surface-Active Classification of Agents by HLB, Newspaper of the Society of Cosmetic Chemists 1 (1949):31). This method allows the determination of reference points which quantify existing balance between the hydrophilic part and the lipophilic part of the molecule of surfactant, and which are related to its solubility in water. The scale varies from 0 to 40: the higher the value of HLB, the bigger is the solubility in water. In 1957, Davies suggested a method based on calculating a value based on the chemical groups of the molecule. The advantage of this method is that it takes into account the effect of stronger and weaker hydrophilic groups. According to the method of Davies:

$$HLB = \Sigma HLB_{groupes\ hydrophiles} - \Sigma HLB_{groupes\ hydrophobes} + 7.$$

Preferred surfactants of the invention are surfactants having a HLB greater than 8, more preferably ranging from 8 to 40, more preferably ranging from 8 to 30. In a preferred embodiment, the surfactant having an HLB greater than 8 is chosen among polyethylene castor oil, polyoxyethylene alkyl ether, polyoxyethylene sorbitan fatty acid esters, polyoxyethylene stearate, sodium lauryl sulfate, sodium docusate, cetrimide, phospholipids, cetylpyridinium chloride, and a mixture thereof. In a more preferred embodiment, the surfactant having an HLB greater than 8 is sodium docusate.

In a particular embodiment, the surfactant having an HLB greater than 8 as disclosed herein is in a concentration from 0.01 to 10 mg/mL, preferably from 0.5 to 8 mg/mL, more preferably from 1 to 5 mg/mL. In a more preferred embodiment, the surfactant having an HLB greater than 8 is in an amount of about 0.5, 0.6, 0.7, 0.8, 0.9, 1.0, 1.1, 1.2, 1.3, 1.4, 1.5, 2.0, 2.5, 3.0, 3.5, 4.0, 4.5, 4.6, 4.7, 4.8, 4.9, 5.0, 5.1, 5.2, 5.3, 5.4, or 5.5 mg per mL of composition. In a further more preferred embodiment, the surfactant having an HLB greater than 8 is in an amount of about 1 or 5 mg per mL of composition or about 1.5 or 7.5 mg per 1.5 mL of composition.

A preferred composition according to the invention is a veterinary composition comprising:
  a concentration from 50 to 300 mg/mL, preferably from 100 to 200 mg/mL, more preferably from 120 to 150 mg/mL of iron element supplied as iron complex as a sole active ingredient as disclosed herein;
  a concentration from 1 to 100 mg/mL, preferably from 5 to 70 mg/mL, preferably from 7 to 60 mg/mL, more preferably from 10 to 50 mg/ml of a water-soluble polymer as disclosed herein;
  a concentration from 1 to 20 mg/mL, preferably from 5 to 10 mg/mL, more preferably from 5 to 8 mg/mL of an organic solvent as disclosed herein; and
  a concentration from 0.01 to 10 mg/mL, preferably from 0.5 to 8 mg/mL, more preferably from 1 to 5 mg/mL of a surfactant having an HLB greater than 8 as disclosed herein.

A more preferred composition according to the invention is a veterinary composition comprising:
  a concentration of about 133.4 mg/mL of iron element supplied as iron complex as a sole active ingredient as disclosed herein;
  a concentration of about 10 or 50 mg/mL of polyvinyl pyrrolidone;
  a concentration of about 6.4 mg/mL of phenol; and
  a concentration of about 1 or 5 mg/mL of sodium docusate.

An even more preferred composition according to the invention is a veterinary composition comprising:
  a concentration from 50 to 300 mg/mL, preferably from 100 to 200 mg/mL, more preferably from 120 to 150 mg/mL of iron element supplied as iron complex as a sole active ingredient as disclosed herein;
  a concentration from 1 to 100 mg/mL, preferably from 5 to 70 mg/mL, preferably from 7 to 60 mg/mL, more preferably from 10 to 50 mg/ml of a water-soluble polymer as disclosed herein;
  a concentration from 1 to 20 mg/mL, preferably from 5 to 10 mg/mL, more preferably from 5 to 8 mg/mL of an organic solvent as disclosed herein;
  a concentration from 1 to 100 mg/mL, preferably from 5 to 70 mg/mL, more preferably from 10 to 50 mg/mL of a pharmaceutically acceptable salt as disclosed herein; and
  a concentration from 0.01 to 10 mg/mL, preferably from 0.5 to 8 mg/mL, more preferably from 1 to 5 mg/mL of a surfactant having an HLB greater than 8 as disclosed herein.

A further even more preferred composition according to the invention is a veterinary composition comprising:
  a concentration of about 133.4 mg/mL of iron element supplied as iron complex as a sole active ingredient as disclosed herein;
  a concentration of about 10 or 50 mg/mL of polyvinyl pyrrolidone.
  a concentration of about 6.4 mg/mL of phenol;
  a concentration of about 10 or 50 mg/mL of sodium chloride; and
  a concentration of about 1 or 5 mg/mL of sodium docusate.

The veterinary composition of the invention as defined herein may also comprise at least one further excipient such as an anti-foaming agent. As a non-limitative example of anti-foaming agent, mentioned be made to soybean lecithins, sorbitan esters, polyol esters, silicone emulsion, simethicone emulsion, propylene glycol monolaurate, propylene glycol monocaprylate, glyceryl monooleate, phospholipids, lauroyl polyoxylglycerides, linoleoyl polyoxylglycerides, oleoyl polyoxylglycerides, or polyoxyethylene alkyl ether. Preferred anti-foaming agents are sorbitan monooleate, propylene glycol monolaurate and simethicone emulsion. In a more preferred embodiment, the antifoaming agent is a simethicone emulsion, which typically comprises about 25 to 35% of simethicone USP by weight. In a specific example, the simethicone emulsion contains the following constituents: polydimethylsiloxane, octamethylcyclotetrasiloxane, methylcellulose, decamethylcyclopentasiloxane, methylated silica and sorbic acid.

The compositions of the present invention as disclosed herein can be prepared by any method known from a skilled person. For instance, the compositions are prepared by providing the iron complex, the water-soluble polymer, the organic solvent, the optional pharmaceutically acceptable salt, the optional surfactant having an HLB greater than 8, and water q.s., mixing said ingredients in an appropriate container. The compositions of the invention may be prepared in advanced and stored in any appropriate container (flask, bottle, etc.). Alternatively, the compositions may be prepared extemporaneously, e.g., by mixing the ingredients shortly before administration.

Application

The compositions of the invention as disclosed herein may be used for the prevention and/or the treatment of any non-human mammal, particularly suffering from iron deficiencies and anemia.

An object of the present invention is therefore a composition as disclosed herein for use for controlling iron deficiencies and/or anaemic states in a non-human mammal.

A further object of the invention is a method for controlling iron deficiencies and/or anaemic states in a non-human mammal, comprising administering en effective amount of a composition as disclosed herein in said non-human mammal.

A further object of the invention is a use of a veterinary composition as disclosed herein for the manufacture of a drug for controlling iron deficiencies and/or anaemic states in a non-human mammal.

As used herein, the expressions "controlling iron deficiencies and/or anaemic states" and "control of iron deficiencies and/or anaemic states" include the prevention and/or the treatment of iron deficiencies and/or anaemic states in a non-human mammal. In an embodiment, iron deficiencies and/or anaemic states are controlled thanks to the iron intake in the non-human mammal in need thereof. In a further embodiment, the iron intake corrects the natural iron deficiencies in the non-human mammal.

As used herein, the terms "treatment" and "control" include, particularly, the preventive treatment of non-human mammals against iron deficiencies and/or anemia states. The preventive treatment of a non-human mammal against a disease designates a treatment made before the non-human mammal suffer from anemia and/or before development of the symptoms or at an early stage of development of the disease, particularly anemia or a disease related to iron-deficiencies.

The term "treatment" also includes the alleviation of the symptoms, as well as a delay, reduction or cure of anemia or a disease related to iron deficiencies. The term "treatment" also includes an increase in the welfare of the treated non-human mammal, allowing thereby a satisfactory growth. It also includes for an increasing of the production of meat.

As used herein, the "diseases related to iron deficiencies" are known from a skilled person. For instance, "diseases related to iron deficiencies" include, without limitation, anemia, infectious diseases, such as coccidiosis, and inflammatory diseases, etc.

As used herein "an effective amount" designates preferably a dose of the composition of the invention which produces a clinical benefit in the treated non-human mammal. Particularly, an effective amount is an amount sufficient to control iron deficiencies, reduce and/or treat anemia.

The compositions of the invention may be formulated as a solution or suspension, or any form suitable for an oral or parenteral administration. The compositions of the invention are preferably administered by an oral or parenteral route, preferably by a parenteral route.

More particularly, the compositions of the invention may be administered parenterally by injection (e.g., intramuscular, subcutaneous, intravenous, or the like), infusion or implantation in dosage forms and formulations, or via suitable delivery devices or implants.

The preferred administration route of the compositions of the invention is by injection. The intramuscular administration route is most preferred.

The compositions of the invention may be administered by injection(s) using techniques and/or devices known per se in the art. In this regard, injection, such as intramuscular injection can be performed with a syringe, a gun, a micro-needle injection device, a needle-free injection device, a pulse device, etc. In a preferred embodiment, injection is performed with a needle injector or a syringe. In another particular embodiment, injection is performed with a needle-free injection device such as a pulse needle-free system, more particularly a spring-powered, battery-powered, or compressed-gas-powered device. Specific examples of needle free technologies are described e.g., in WO2006/058426, WO2007/140610, or WO2009/111794. A preferred needle-free injection device for use in the present invention is AcuShot™ needle free technology described in the international patents WO2006/058426 and WO2007/140610. Intramuscular injection may be made in any muscle.

The compositions of the invention are more preferably administered by a single injection.

A particular object of the invention thus resides in a veterinary composition for use as disclosed herein, in which said composition is administered by injection, preferably by intramuscular injection, more preferably by a single injection.

A further particular object of the invention resides in a method for controlling irons deficiencies and/or anaemic states in a non-human mammal, comprising an intramuscular injection to said non-human mammal an effective amount of a veterinary composition as disclosed herein.

The present invention may be used in any non-human mammals, including porcine, ovine, bovine, canine or feline, preferably livestock, breeding animals, companion animals, and laboratory animals. Livestock and breeding animals include mammals such as, for example, cattle, horses, sheep, pigs, goats, camels, water buffalos, donkeys, rabbits, fallow deer, reindeer, fur bearers such as, for example, mink, chinchilla or raccoon. Companion animals include such as, for example, horses, dogs and cats. Laboratory animals and experimental animals include such as, for example, mice, rats, guinea pigs, or golden hamsters. Particular emphasis may be placed on pigs, cattle, sheep and dogs in all species, subspecies and breeds. It may be used in adults or young animals, such as newborn to 10 days old non-human mammals.

A preferred object of the invention is a veterinary composition for use as disclosed herein, in which said non-human mammal is a porcine, an ovine, a bovine, a canine, or a feline, preferably a piglet.

The invention is particularly suited to treat young piglets, between newborn and 3 days after birth, which usually have a weight of between 0.40 to 5 kg. More particularly, for treating such population, there is no need to dilute the compositions, nor to weight the animal for adjustment.

A preferred embodiment of the invention is a veterinary composition as disclosed herein for use for controlling iron deficiencies and/or anaemic states in a piglet, in which 1.5 mL of said composition is administered by a single intramuscular injection in said piglet.

What is claimed is:

1. A veterinary composition comprising an aqueous colloidal solution of beta-ferric oxyhydroxide, dextran glucoheptonic acid and polyvinyl pyrrolidone.

2. The veterinary composition according to claim 1, wherein said polyvinyl pyrrolidone is in a concentration from 1 to 100 mg/mL.

3. The veterinary composition according to claim 1, further comprising an organic solvent.

4. The veterinary composition according to claim 3, wherein said organic solvent is in a concentration from 1 to 20 mg/mL.

5. The veterinary composition according to claim 1, further comprising a pharmaceutically acceptable salt and/or a surfactant having an HLB greater than 8.

6. The veterinary composition according to claim 5, wherein said pharmaceutically acceptable salt is selected from the group consisting of calcium gluconate, calcium phosphate, calcium chloride, calcium sulfate, calcium carbonate, magnesium gluconate, magnesium phosphate, magnesium chloride, magnesium sulfate, magnesium carbonate, potassium phosphate, potassium gluconate, potassium chloride, potassium sulfate, potassium carbonate, sodium gluconate, sodium chloride, sodium carbonate, sodium lactate, sodium propionate, sodium phosphate, sodium citrate, sodium sulfate, ammonium chloride, and ammonium carbonate, and a mixture thereof.

7. The veterinary composition according to claim 5, wherein said pharmaceutically acceptable salt is in a concentration from 1 to 100 mg/mL.

8. The veterinary composition according to claim 5, wherein said surfactant having an HLB greater than 8 is selected from the group consisting of polyethylene castor oil, polyoxyethylene alkyl ether, polyoxyethylene sorbitan fatty acid esters, polyoxyethylene stearate, sodium lauryl sulfate, sodium docusate, cetrimide, phospholipids, cetylpyridinium chloride, and a mixture thereof.

9. The veterinary composition according to claim 5, wherein said surfactant having an HLB greater than 8 is in a concentration from 0.01 to 10 mg/mL.

10. The veterinary composition according to claim 1, wherein the iron supplied as an aqueous colloidal solution of beta-ferric oxyhydroxide and dextran glucoheptonic acid is in a concentration from 50 to 300 mg/mL iron element.

11. A method for controlling iron deficiencies and/or anaemic states in a non-human mammal, comprising administering an effective amount of a veterinary composition as defined in claim 1.

12. The method for controlling iron deficiencies and/or anaemic states in a non-human mammal according to claim 11, wherein said non-human mammal is a porcine, an ovine, a bovine, a canine, or a feline.

13. The method for controlling iron deficiencies and/or anaemic states in a non-human mammal according to claim 10, wherein said composition is administered by injection.

14. The veterinary composition according to claim 1, wherein said polyvinyl pyrrolidone is in a concentration from 5 to 70 mg/mL.

15. The veterinary composition according to claim 1, wherein said polyvinyl pyrrolidone is in a concentration from 7 to 60 mg/mL.

16. The veterinary composition according to claim 1, wherein said polyvinyl pyrrolidone is in a concentration from 10 to 50 mg/mL.

17. The veterinary composition according to claim 3, wherein the organic solvent is selected from the group consisting of methanol, ethanol, butanol, ethylene glycol, polyethylene glycol, propylene glycol, polypropylene glycol, glycerol, phenol, benzyl alcohol, phenylethanol, phenoxyethanol, ethyl acetate, butyl acetate benzyl benzoate, ethyl oleate, diethylene glycol monoethyl ether, diethylene glycol monobutyl ether, dipropylene glycol monomethyl ether, acetone, methyl ethyl ketone, glycerol formal, 2,2-dimethyl-4-hydroxymethyl-1,3-dioxolane, N-methyl-pyrrolidone, 2-pyrrolidone, N,N-dimethylacetamide, glycofurol, dimethyl-isosorbitol, lauroglycol, propylene carbonate, octyldodecanol, dimethylformamide, and a mixture thereof.

18. The veterinary composition according to claim 17, wherein the organic solvent is phenol.

19. The veterinary composition according to claim 4, wherein said organic solvent is in a concentration from 5 to 10 mg/mL.

20. The veterinary composition according to claim 19, wherein said organic solvent is in a concentration from 5 to 8 mg/mL.

21. The veterinary composition according to claim 6, wherein said pharmaceutically acceptable salt is sodium chloride.

22. The veterinary composition according to claim 7, wherein said pharmaceutically acceptable salt is in a concentration from 5 to 70 mg/mL.

23. The veterinary composition according to claim 22, wherein said pharmaceutically acceptable salt is in a concentration from 10 to 50 mg/mL.

24. The veterinary composition according to claim 8, wherein said surfactant having an HLB greater than 8 is sodium docusate.

25. The veterinary composition according to claim 9, wherein said surfactant having an HLB greater than 8 is in a concentration from 0.5 to 8 mg/mL.

26. The veterinary composition according to claim 25, wherein said surfactant having an HLB greater than 8 is in a concentration from 1 to 5 mg/mL.

27. The veterinary composition according to claim 10, wherein the iron supplied as an aqueous colloidal solution of beta-ferric oxyhydroxide and dextran glucoheptonic acid is in a concentration from 100 to 200 mg/mL iron element.

28. The veterinary composition according to claim 27, wherein the iron supplied as an aqueous colloidal solution of beta-ferric oxyhydroxide and dextran glucoheptonic acid is in a concentration from 120 to 150 mg/mL iron element.

29. The veterinary composition according to claim 1, comprising:
a concentration of about 133.4 mg/mL of iron element supplied as an aqueous colloidal solution of beta-ferric oxyhydroxide and dextran glucoheptonic acid as a sole active ingredient;
a concentration of about 10 mg/mL of polyvinyl pyrrolidone; and
a concentration of about 6.4 mg/mL of phenol.

30. The method for controlling iron deficiencies and/or anaemic states in a non-human animal according to claim 11, wherein said non-human mammal is a piglet.

* * * * *